(12) United States Patent
Kent et al.

(10) Patent No.: US 7,125,416 B2
(45) Date of Patent: Oct. 24, 2006

(54) LIGHT THERAPY DEVICE

(75) Inventors: Marsha Kent, Austin, TX (US); Ron Lynch, Austin, TX (US)

(73) Assignee: Sylmark Holdings Limited (IE)

( * ) Notice: Subject to any disclaimer, the term of this patent is extended or adjusted under 35 U.S.C. 154(b) by 181 days.

(21) Appl. No.: 10/780,530

(22) Filed: Feb. 17, 2004

(65) Prior Publication Data

US 2005/0182460 A1    Aug. 18, 2005

(51) Int. Cl.
*A61N 5/01* (2006.01)

(52) U.S. Cl. .......................................... 607/88

(58) Field of Classification Search ............. 607/88–94
See application file for complete search history.

(56) References Cited

U.S. PATENT DOCUMENTS

| | | | |
|---|---|---|---|
| 4,907,132 A | 3/1990 | Parker | |
| 5,000,752 A | 3/1991 | Hoskin et al. | |
| 5,358,503 A | 10/1994 | Bertwell et al. | |
| 5,851,225 A | 12/1998 | Lawandy | |
| 5,913,883 A * | 6/1999 | Alexander et al. | 607/88 |
| 5,944,748 A | 8/1999 | Mager et al. | |
| 5,957,960 A | 9/1999 | Chen et al. | |
| 5,997,569 A | 12/1999 | Chen et al. | |
| 6,045,575 A | 4/2000 | Rosen et al. | |
| 6,063,108 A | 5/2000 | Salansky et al. | |
| 6,096,066 A | 8/2000 | Chen et al. | |
| 6,221,095 B1 | 4/2001 | Van Zuylen et al. | |
| 6,238,424 B1 * | 5/2001 | Thiberg | 607/88 |
| 6,306,130 B1 | 10/2001 | Anderson et al. | |
| 6,454,791 B1 * | 9/2002 | Prescott | 607/89 |
| 6,471,716 B1 * | 10/2002 | Pecukonis | 607/89 |
| 6,494,900 B1 | 12/2002 | Salansky et al. | |
| 6,497,702 B1 | 12/2002 | Bernaz | |
| 6,596,016 B1 | 7/2003 | Vreman et al. | |
| 6,602,275 B1 * | 8/2003 | Sullivan | 607/88 |
| 6,743,249 B1 * | 6/2004 | Alden | 607/88 |
| 6,802,853 B1 * | 10/2004 | Osendowski | 607/89 |
| 6,811,563 B1 * | 11/2004 | Savage et al. | 607/88 |
| 6,860,896 B1 * | 3/2005 | Leber et al. | 607/1 |
| 2001/0008973 A1 | 7/2001 | Van Zuylen et al. | |
| 2002/0143373 A1 * | 10/2002 | Courtnage et al. | 607/91 |
| 2002/0198575 A1 | 12/2002 | Sullivan | |
| 2003/0009205 A1 | 1/2003 | Biel | |
| 2003/0187486 A1 * | 10/2003 | Savage et al. | 607/89 |

* cited by examiner

*Primary Examiner*—Henry M Johnson, III
(74) *Attorney, Agent, or Firm*—Kathy Mojibi Kavcioglu

(57) ABSTRACT

A therapeutic device is provided having a housing unit and a LED pad, wherein in a first configuration, the housing unit is attached to the LED pad and in the second configuration, the housing unit is detached from the LED pad. The housing unit and LED pad can be removably attached using known fasteners, such as VELCRO. Alternatively, the housing unit and LED pad can be press fitted.

18 Claims, 4 Drawing Sheets

LIGHT THERAPY DEVICE

FIELD OF INVENTION

The present invention relates generally to therapeutic devices for treatment of muscular and joint pains, and more particularly to portable therapeutic devices utilizing light emitting diodes for light and heat radiation.

BACKGROUND OF THE INVENTION

Light therapy devices have been used for treatment of muscular and joint pains. Typically, the light therapy device includes a rigid housing having an applicator end. The applicator end is integrally attached to the housing thus forming a self-contained unit. Light emitting diodes ("LEDs") are positioned in the housing such that they emit light from the applicator end of the device. The housing generally also contains a battery pack and a processor for controlling the frequency and duration of light delivery. Other electrical components may be provided in the housing depending on the electronic features of the device.

To operate the known therapeutic device, a user grasps the rigid housing of the device and positions the applicator end of the device on the area to be treated. The LEDS are then energized causing light and heat radiation at the applicator end of the device. For effective treatment, the radiation must be applied for a specified time period. This requires the device to be held in place by the user. Depending on the area and problem that is treated, the duration of the treatment can vary from a few minutes to several hours.

A disadvantage of the known therapeutic device is that it is inconvenient for the user to hold the device in position for an extended period of time. This is particularly true if the area to be treated is difficult to reach, such as the user's back or feet. In this regard, it would be desirable to provide a device that would be more conveniently held in position for an extended period of time without requiring the user to hold it.

Some known devices use straps attached to the housing to hold the therapeutic device in position for extended periods of time. The disadvantage of such devices is that strapping a bulky housing to the user could be uncomfortable. For example, a user who straps the housing to his back, may not be able to comfortably lay down. Similarly, a user who straps the device to the back of her thigh, may not be able to sit comfortably.

A further disadvantage of the known devices is that, depending on the area treated, once the device is strapped, a user can no longer see the control display. For example, if the user straps the unit to his back, he can no longer see the face of the housing and will be unable to monitor the display. Furthermore, to change a setting, the user will be required to unstrap the device to access the control panel, and then restrap the unit once the setting has been changed. It would be desirable, to provide a unit that could comfortably be applied to the area for treatment while allowing the user convenient access to the control panel.

SUMMARY OF PREFERRED EMBODIMENTS

A therapeutic device is provided having a housing unit and a LED pad, wherein in a first configuration, the housing unit is attached to the LED pad and in the second configuration, the housing unit is detached from the LED pad. The housing unit and LED pad can be removably attached using known fasteners, such as VELCRO. Alternatively, the housing unit and LED pad can be press fitted.

DETAILED DESCRIPTION OF PREFERRED EMBODIMENTS

Figure 1:
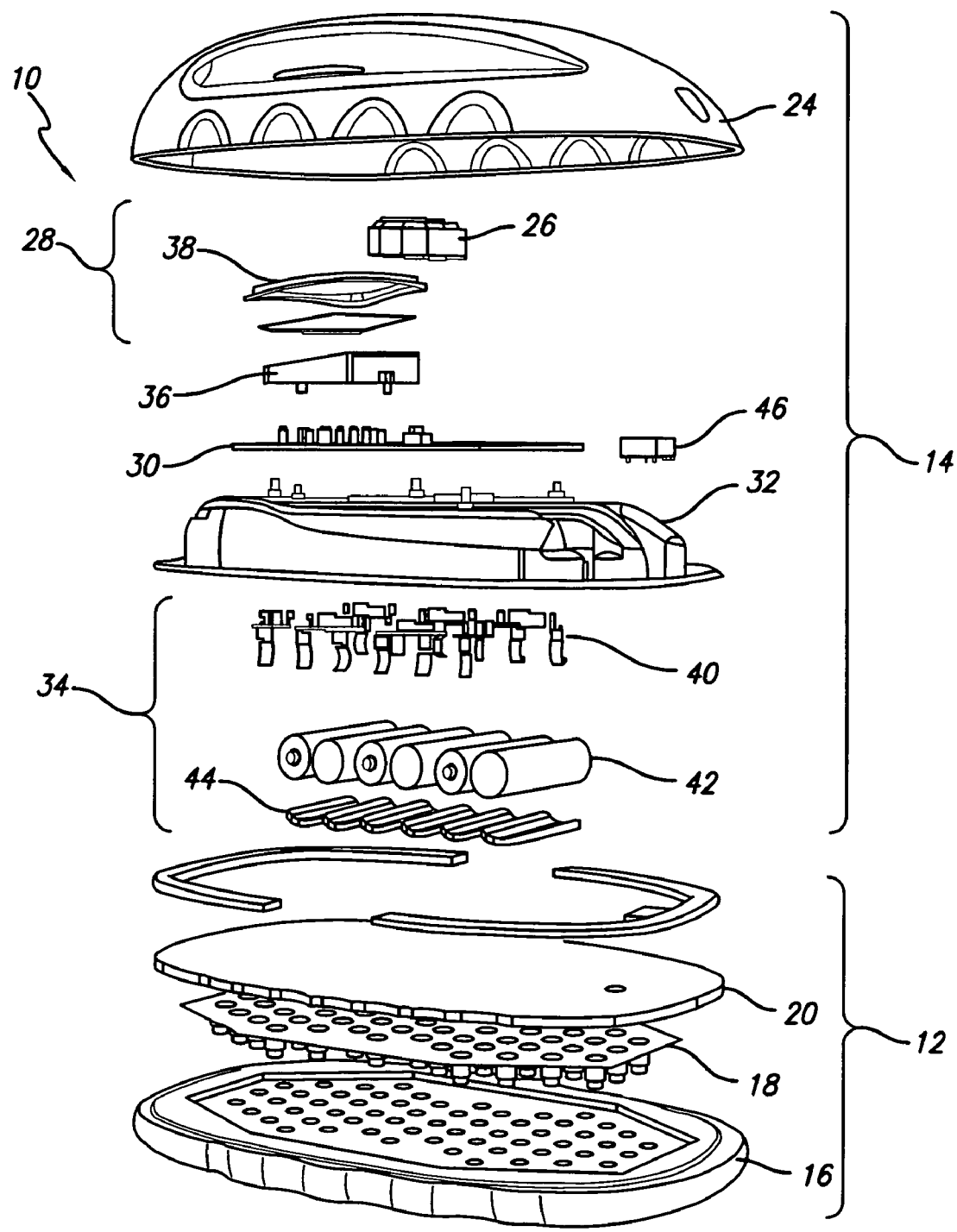
FIG. 1 is an exploded view of a preferred embodiment of the light therapy device of the present invention.

As shown in FIG. 1, a preferred embodiment of the light therapy device 10 of the present invention includes an LED pad 12 and a housing unit 14. The LED pad 12 preferably comprises a flexible base 16, an LED array 18 and a back support member 20. The flexible base 16 includes a plurality of apertures 22, each aperture preferably dimensioned to receive a single LED therein. The depth of each aperture is coordinated with the height of the LEDs, so that the upper ends of the LEDs are essentially flush with or slightly recessed relative to the upper surface 24 of the LED pad 12. The flexible base 16 is preferably made of a material having elastic yield, and more preferably, is made of a flexible foam. The elastic nature of the base 16 allows the flexible pad 12 to conform to the shape of the treatment area, providing a comfortable fit for the user.

In a preferred embodiment of the invention, the LED array 18 is polychromatic, including infrared and visible LEDs. The visible LEDs can be of any color within the visible spectrum. In a preferred embodiment of the invention, the majority of the visible LEDs are red.

The LED array 18 is preferably sandwiched between the flexible base 16 and the back support member 20. Alternatively, the LED array 18 can be integrally attached to the back support member 20.

The housing unit 14 preferably comprises a top shell 24, control panel 26, a display unit 28, a controller 30, an inner tray 32 and a battery pack unit 34. In a preferred embodiment of the invention, the controller 30 is operatively connected to the LED array 18 and, in conjunction with the control panel 26 and display unit 28, enables the user to control the operation of the LED array. For example, in one embodiment of the invention, the user will be able to operate the unit at a "Low," "Medium" and "High" frequency setting. When the "Low" setting is selected, the display unit 28 displays a setting identifier, such as "LOW" and the controller 30 signals the LED array to operate at the selected "LOW" frequency. The controller 30 may also be used to program the duration of the treatment, to track the duration of use, temperature or other such information.

The display unit 28 can be any known type of display that provides users with setting indicators. In a preferred embodiment of the invention, the display unit includes a liquid crystal display 36 and a lens 38 made of a clear, rigid plastic.

Battery pack unit 34 is preferably any suitable conventional battery pack having sufficient electrical energy storage capacity to support illumination of LED pad 12 for the treatment times selected on controller 30. In the embodiment shown, the battery pack includes battery clips 40 for securely retaining the batteries 42 and a battery cover 44. In addition to the battery pack, or in place of it, electric power to the LED pad 12 can be provided by a line plugged into a power jack 46.

Figure 2:
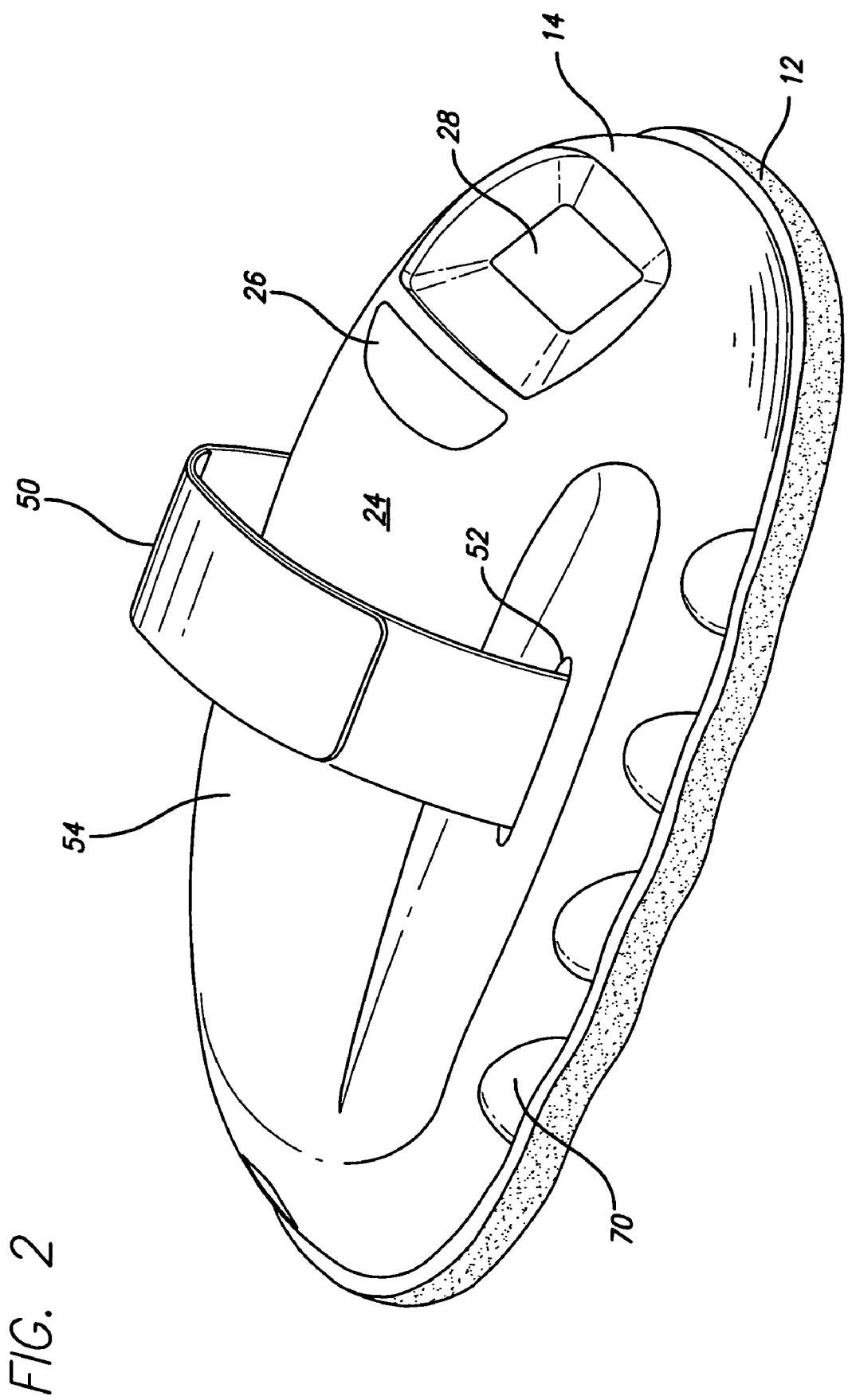
FIG. 2 is a perspective view of a preferred embodiment of the light therapy device of the present invention depicting the flexible LED pad attached to the housing unit.

In a preferred embodiment of the invention, the therapeutic device 10 has at least two configurations. In a first configuration, as shown in FIG. 2, the LED pad 12 is attached to the housing unit 14. To use the device 10 in the first configuration, a user, while holding the top shell 24, applies the LED pad 12 to the area to be treated. To facilitate the user's grasp of the top shell 24, a flexible handle 50 is provided. To grasp the top shell 24, the user slides his hand under handle 50 such that the palm of the user's hand rests on the top shell 24. In a preferred embodiment, the handle 50 is a strap threaded through slots 52 in the top shell 24. The straps are preferably adjustable to firmly, yet comfortably, maintain the user's palm against the top shell 24. In one embodiment, the handle 50 comprises two straps that are adjustably fastened together. The two straps can be fastened using VELCRO or any other known fasteners. In another preferred embodiment, the handle is a single strap made of an elastic material, thereby eliminating the need for using fasteners.

The therapeutic device is ergonomically designed to maximize the user's comfort. In a preferred embodiment of the invention, the surface 54 of the top shell 24 is shaped to conform to a user's palm for a more comfortable fit. The buttons of the control panel 26 are positioned to be within the reach of the user's fingers when the user's hand is properly positioned under handle 50. The display unit 28 is positioned to allow the user to see the display when the device is in use. To avoid the user's hand from blocking the display unit, the control panel is preferably positioned between the handle 50 and the display unit 28.

Figure 3:
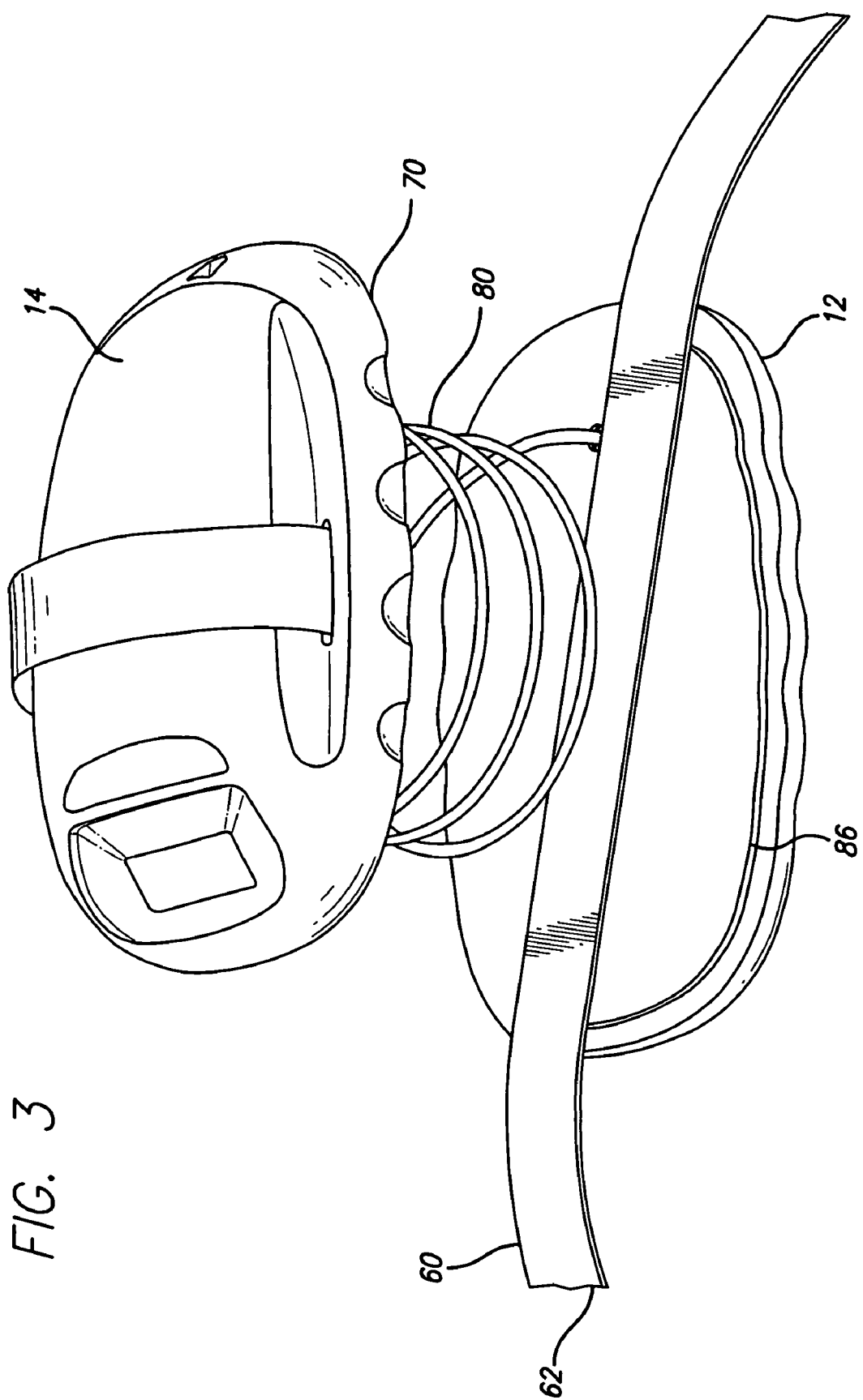
FIG. 3 is a perspective view of a preferred embodiment of the light therapy device of the present invention depicting the flexible LED pad detached from the housing unit.
Figure 4:
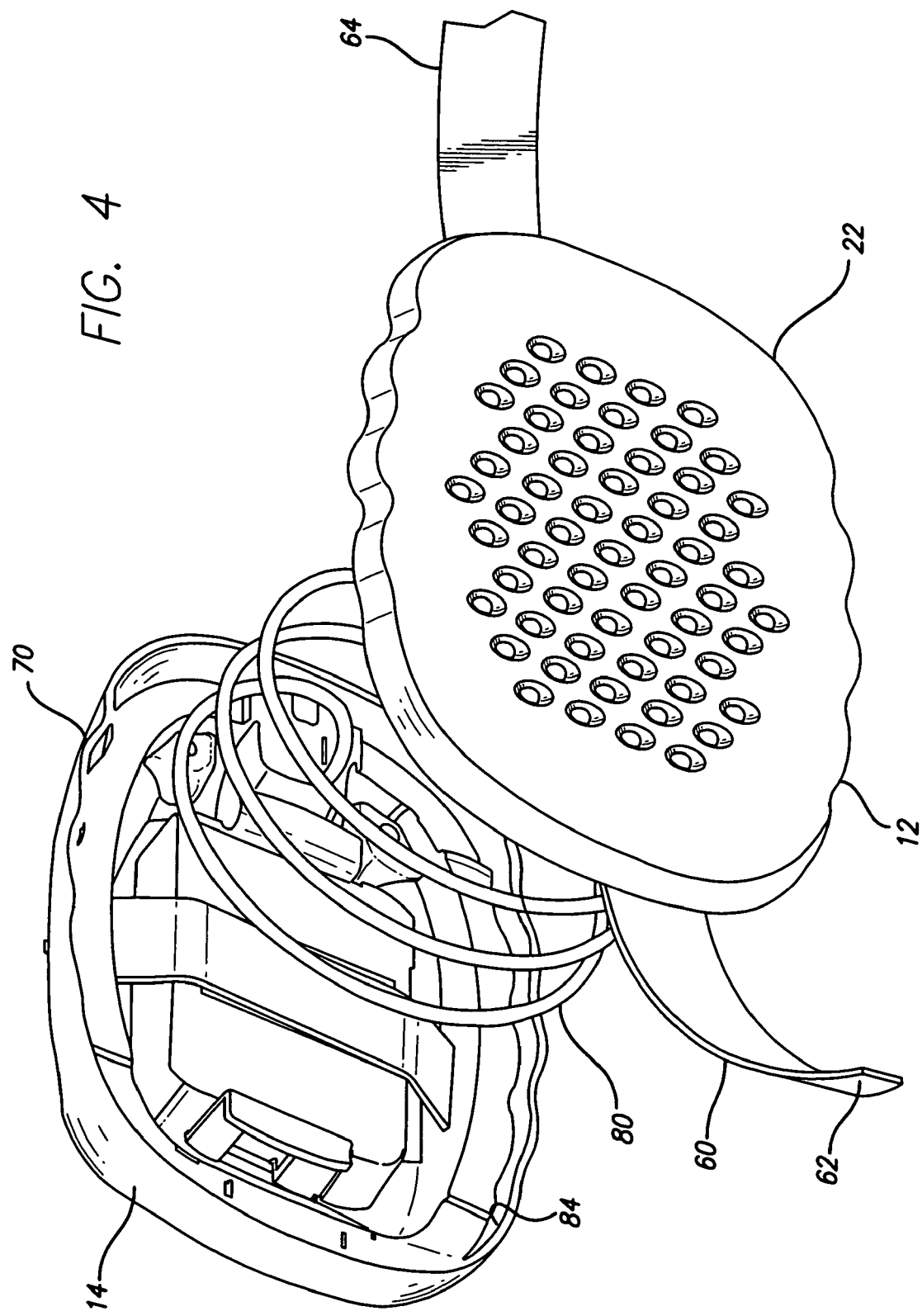
FIG. 4 is another perspective view of the light therapy device depicting the flexible LED pad detached from the housing unit.

In a second configuration, as shown in FIGS. 3 and 4, the LED pad 12 is detachable from the housing unit 14. To use the device in the second configuration, the housing unit 14 is separated from the LED pad 12 and the LED pad 12 alone is applied to the area to be treated. In a preferred embodiment of the invention, the LED pad 12 is sized to allow a user to grasp the edges and apply the pad 12 to the area to be treated. In a more preferred embodiment of the invention, the LED pad 12 can be applied to the area to be treated using strap 60. The length of strap 60 is selected to accommodate the largest circumference of a user's body. For example, if the LED pad 12 is applied to the back, the strap should be long enough to wrap around the user's body. Strap 60 is configured to allow ends 62, 64 to be adjustably fastened to each other. In a preferred embodiment of the invention, the strap ends 62, 64 are fastened by VELCRO. However, any known fastener can be used.

The LED pad 12 is sufficiently thin and flexible such that it does not interfere with the user's comfort when the LED pad 12 is positioned between the user and a hard surface. For example, if the LED pad is applied to the user's back, the device is configured to allow the user to comfortably lie down. Similarly, if the LED pad 12 is strapped to the back of the user's thigh, the user can comfortably sit down.

The electric energy from the battery pack or other power source is delivered to the LED pad 12 via line 80. Similarly, any signals from the controller 30 can be delivered to the LED pad 12 via line 80 or a separate line. Line 80 is preferably made of a flexible electrical cable that is attached at one end to the LED pad 12 and at the other end to the electrical circuitry of the housing unit 14. The length of line 80 is selected to allow a user to position the housing unit 14 on a nearby surface while applying the LED pad 12 to the area to be treated. By separating the housing unit 14 from the LED pad 12, the user can continue to monitor the display unit 28 even when the LED pad 12 is attached to an area that the user cannot see, such as the user's back side. For example, if the LED pad 12 is strapped to the user's shoulder, the user can conveniently position the housing unit 14 so that the display unit 28 is visible and the control panel 26 is accessible. The second configuration allows the user to change the control panel settings while the LED pad remains strapped to the treatment area. Thus, the user will have continuous treatment while adjusting the control panel settings.

To transition between the first and second configurations, the LED pad 12 of the therapeutic device 10 is preferably removably attached to housing unit 14. In a preferred embodiment of the invention, the LED pad 12 is press fitted to the housing unit 14. In this regard, the housing unit 14 has a lip 84 (shown in FIG. 4) dimensioned to receive a protrusion 86 (shown in FIG. 3) on the LED pad 12. The lip 84 and protrusion 86 are dimensioned such that when the LED pad 12 pressed into the housing unit 14, the lip 84 firmly receives the protrusion 86, thus holding the LED pad 12 in place. In a preferred embodiment of the invention, the edging of lip 84 has a scalloped edge 70 which provides further frictional force to attach the LED pad 12 to the housing unit 14.

In another preferred embodiment of the invention, the LED pad 12 is removably attached to the housing unit 14 using known fasteners. For example, in one embodiment of the invention, VELCRO strips 76 are attached to the back support member 20 of the LED pad 12, corresponding VELCRO strips (not shown) are attached to the housing unit 14, and the LED pad 12 is attached to the housing unit 14 by fastening the VELCRO strips. The use of VELCRO strips is exemplary. It is envisioned that many other known fasteners can be used to removably attach the LED pad to the housing unit.

As described above, the therapeutic device of the present invention can be used in a first configuration wherein the LED pad is attached to the housing unit and a second configuration wherein the LED pad is detached from the housing unit. When not in use, the device can be stored in the first configuration. In this regard, a convenient storage configuration is provided which allows for safe storage of the LED pad when the device is not in use. Furthermore, in the storage (first) configuration, line 80 and strap 60 is conveniently stored in the housing unit 14, protecting the line and strap from deterioration caused by the elements.

Although the above embodiments are representative of the present invention, they are exemplary embodiments. Those skilled in the art may now make numerous uses of, and departures from, the above-described embodiments without departing from the inventive concepts disclosed herein. Accordingly, the present invention is to be defined by the scope of the claims and their equivalents.

What is claimed is:

1. A therapeutic device, comprising:
a housing unit defining a slot therein, the housing unit having a handle, the handle comprising a strap threaded through the slot;
a LED pad having a strap separate from the handle, the housing unit defining an opening therein, the opening configured to receive the LED pad;
an electrical line operatively connecting the LED pad to the housing unit;

a first configuration wherein the housing unit is removably attached to the LED pad, and the electrical line and LED strap are stored in the housing unit; and a second configuration wherein the housing unit is detached from the LED pad.

2. The therapeutic device of claim 1 wherein the LED pad is removably attached to the housing unit by a hook and loop fastener.

3. The therapeutic device of claim 1 wherein the LED pad is press fitted to the housing unit.

4. The therapeutic device of claim 3 wherein the housing unit has a scalloped lip and the LED pad has a scalloped protrusion corresponding to the scalloped lip, and wherein the scallop lip securely receives the scalloped protrusion therein.

5. The therapeutic device of claim 1 wherein the housing unit comprises a top shell, a control panel and a display unit, wherein the top shell is configured to the shape of a user's hand, and the control panel is positioned between the handle and the display unit such that the control panel is accessible to a user's fingers when the user's hand is positioned under the handle, and the display unit is visible to the user when the user's hand is positioned under the handle.

6. A therapeutic device comprising a housing unit and a LED pad, wherein the housing unit defines an opening and the opening is configured to receive the LED pad, wherein in a first configuration, the housing unit is removably attached to the LED pad, and in a second configuration, the LED pad is detached from the housing unit.

7. The therapeutic device of claim 6 wherein the housing unit has a handle and the LED pad has a strap separate from the handle.

8. The therapeutic device of claim 7 wherein the handle is elastic.

9. The therapeutic device of claim 7 wherein the handle comprises a strap threaded through a slot in the housing unit.

10. The therapeutic device of claim 7 wherein the LED pad is attached to the housing unit via an electrical line.

11. The therapeutic device of claim 7 wherein in the first configuration, the electrical line and the strap are stored in the opening of the housing unit.

12. The therapeutic device of claim 7 wherein the housing unit comprises a top shell, a control panel and a display unit, wherein the top shell is configured to the shape of a user's hand, and the control panel is positioned between the handle and the display unit such that the control panel is accessible to a user's fingers when the user's hand is positioned under the handle, and the display unit is visible to the user when the user's hand is positioned under the handle.

13. The therapeutic device of claim 6 wherein the LED pad is press fitted to the housing unit.

14. The therapeutic device of claim 13 wherein the housing unit has a scalloped lip and the LED pad has a scalloped protrusion corresponding to the scalloped lip, and wherein the scallop lip securely receives the scalloped protrusion therein.

15. The therapeutic device of claim 6 wherein the LED pad is removably attached to the housing unit by a hook and loop fastener.

16. A therapeutic device, comprising:

a housing unit defining having a handle;

a LED pad having a strap separate from the handle, wherein the housing unit defines an opening therein, and wherein the opening is configured to receive the LED pad;

an electrical line operatively connecting the LED pad to the housing unit;

a first configuration wherein the housing unit is removably attached to the LED pad, and the electrical line and LED strap are stored in the housing unit; and a second configuration wherein the housing unit is detached from the LED pad.

17. The therapeutic device of claim 16 wherein the LED pad is removably attached to the housing unit by a hook and loop fastener.

18. The therapeutic device of claim 17 wherein the LED pad is press fitted to the housing unit.

* * * * *